(12) United States Patent
Cooper et al.

(10) Patent No.: US 8,409,251 B2
(45) Date of Patent: Apr. 2, 2013

(54) SUTURE ANCHOR AND DRIVER

(75) Inventors: John Joseph Cooper, Crewe (GB); Russell David Waters, Knutsford (GB)

(73) Assignee: Biocomposites Limited, Keele, Staffordshire (GB)

( * ) Notice: Subject to any disclaimer, the term of this patent is extended or adjusted under 35 U.S.C. 154(b) by 712 days.

(21) Appl. No.: 12/094,753

(22) PCT Filed: Nov. 27, 2006

(86) PCT No.: PCT/GB2006/004413
§ 371 (c)(1),
(2), (4) Date: May 22, 2008

(87) PCT Pub. No.: WO2007/063285
PCT Pub. Date: Jun. 7, 2007

(65) Prior Publication Data
US 2008/0306511 A1    Dec. 11, 2008

(30) Foreign Application Priority Data
Nov. 30, 2005    (GB) .................................. 0524360.5

(51) Int. Cl.
*A61B 17/04* (2006.01)
(52) U.S. Cl. ........................................................ 606/232
(58) Field of Classification Search .................... 606/72, 606/73, 232, 300–331; 623/13.14
See application file for complete search history.

(56) References Cited

U.S. PATENT DOCUMENTS

| 5,100,417 | A |   | 3/1992 | Cerier et al. |
| 5,690,676 | A | * | 11/1997 | DiPoto et al. ................. 606/232 |
| 5,733,307 | A | * | 3/1998 | Dinsdale ....................... 606/232 |
| 6,517,542 | B1 | * | 2/2003 | Papay et al. ................... 606/232 |
| 6,840,953 | B2 | * | 1/2005 | Martinek ....................... 606/232 |
| 6,890,354 | B2 | * | 5/2005 | Steiner et al. ............. 623/13.14 |
| 7,588,587 | B2 | * | 9/2009 | Barbieri et al. ............... 606/232 |
| 7,713,285 | B1 | * | 5/2010 | Stone et al. ................... 606/232 |
| 7,780,701 | B1 | * | 8/2010 | Meridew et al. .............. 606/232 |
| 2005/0222619 | A1 | * | 10/2005 | Dreyfuss et al. ............. 606/232 |
| 2006/0079904 | A1 | * | 4/2006 | Thal ................................ 606/72 |
| 2006/0253119 | A1 |   | 11/2006 | Berberich et al. |
| 2010/0185238 | A1 | * | 7/2010 | Cauldwell et al. ........... 606/232 |

FOREIGN PATENT DOCUMENTS

| DE | 10220021885.7 | * | 5/2005 |
| EP | 0829233 |   | 3/1998 |
| WO | 9852471 |   | 11/1998 |
| WO | 03070108 |   | 8/2003 |
| WO | 2004062507 |   | 7/2004 |

* cited by examiner

*Primary Examiner* — Melanie Tyson
(74) *Attorney, Agent, or Firm* — Chernoff Vilhauer McClung & Stenzel LLP

(57) ABSTRACT

A suture anchor assembly with an anchor and a driver locatable in an axial longitudinal opening in the anchor. A suture is provided extending through the opening and outside of the anchor at its distal end, and passing proximally along longitudinal grooves on the outside of the anchor. A recess is provided in the longitudinal opening of the suture body and a groove formation is provided in the drive part of the driver to locate the suture therein.

24 Claims, 10 Drawing Sheets

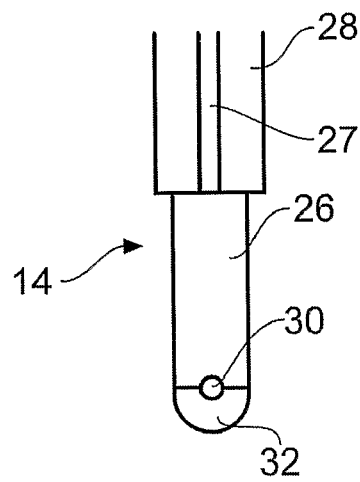 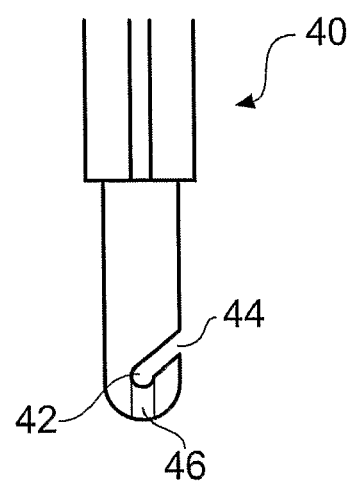 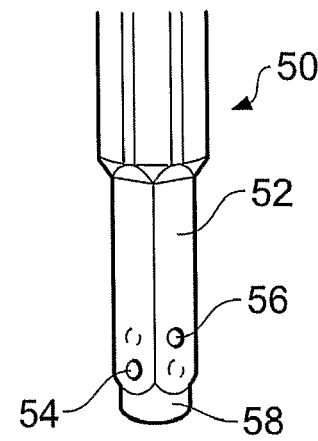
Fig. 6  Fig. 7  Fig. 8
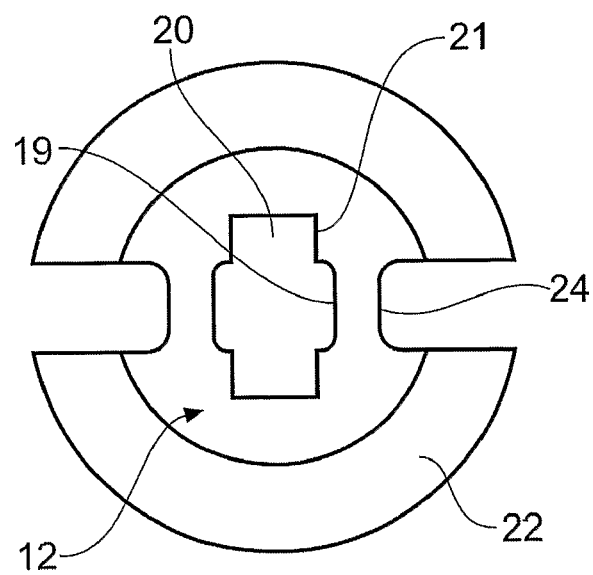
Fig. 9

SUTURE ANCHOR AND DRIVER

This is a national stage application filed under 35 USC 371 based on International Application No. PCT/GB2006/004413 filed Nov. 27, 2006, and claims priority under 35 USC 119 of United Kingdom Patent Application No. 0524360.5 filed Nov. 30, 2005.

This invention concerns a suture anchor assembly, anchors and drivers usable in such an assembly, and a method of attaching a suture to a bone.

There are many surgical procedures where sutures are required to be attached to bone in order to secure the adjacent soft tissue to the bone. These procedures include the repair and/or re-attachment of torn or damaged tendons and ligaments in the shoulder, knee, ankle, foot and hand. A wide variety of suture anchors are available to satisfy this requirement. They are manufactured from a range of different materials including both metals and resorbable polymers. They can have a wide range of geometric configurations and modes of deployment and action.

Metallic anchors have the main advantage of high mechanical strength. They are less likely to fail, either during insertion or when subsequently mechanically loaded, when compared to their polymer counterparts. Metals, however, do have a number of disadvantages. They can cause fretting and premature failure of the suture where it passes through the eyelet. They interfere with magnetic resonance imaging (MRI), which can make assessment of the surgical site by this technique difficult if not impossible. They are permanent implants that can lead to long-term clinical problems. Additionally they can make any future surgery at the same site difficult.

Bioabsorbable polymers can overcome many of the problems associated with metals although their lower mechanical strength can limit their functionality. The suture eyelet, which is often at the proximal end of the anchor, is a weak point that can fail either by breaking away from the body of the anchor or by the suture pulling through the eyelet when tension is applied to the suture.

Screw-in type suture anchors, whether metal or polymer, offer a number of advantages compared to anchors that are pushed or punched in. Their depth within the bone can be easily and accurately adjusted either forwards or backwards. They can be removed completely from the bone without damaging adjacent tissue simply by screwing out. They have improved holding power compared to push-in or punch-in type anchors particularly in poor quality bone and their holding power within the bone can be increased by increasing their length and/or thread depth.

Twin eyelet suture anchors, as opposed to anchors that have a single eyelet, provide two attachment points per deployed anchor. This helps to distribute the load of the sutures onto the soft tissue thus reducing the potential for the sutures cutting through the tissue during physiological loading, which can often be the main mode of failure in the repair. Multiple sutures per anchor also provide the surgeon with more versatile suture placement options.

According to the present invention there is provided a suture anchor assembly, the assembly including an anchor locatable in a bone, and a driver selectively engageable with the anchor to enable rotation of the anchor, the anchor including a body with a screw thread on the exterior thereof, a longitudinal opening extending through the body and having a non circular cross section, at least one exterior opening being provided extending through the anchor from the longitudinal opening to the exterior of the anchor, the driver including a drive part locatable within the longitudinal opening of the anchor and profiled such that rotation of the driver causes rotation of the anchor.

The driver may also include an engagement means for receiving a loop of suture with the ends of the loop extendable from the engagement means, each end on a generally opposite side of the exterior of the anchor to the other when the drive part is located in the longitudinal opening of the anchor, such that when the driver is withdrawn proximally from the anchor a loop of suture extends proximally out of the longitudinal opening as well as the suture ends extending externally of the anchor.

A recess formation may be provided on the outside of the anchor which can receive two lengths of suture extending to the proximal end of the anchor. The recess formation may be dimensioned such that the suture does not extend substantially outwardly beyond the thread root when located in said formation, or may be dimensioned such that the suture does extend outwardly therefrom to some extent.

The recess formation may extend from the distal end of the anchor longitudinal opening to the proximal end of the anchor.

The recess formation may include a longitudinal groove in the outside of the anchor body, and may include a pair of longitudinal grooves, which grooves may be substantially diametrically opposite each other.

The longitudinal opening in the anchor may be generally rectangular in cross section. Alternatively, the longitudinal opening in the anchor may be generally triangular in cross section. Recesses may be provided in one or more of the sides of the longitudinal opening for at least part of the length of the opening, to at least partially locate a suture in the recess.

The screw thread may be helical, and may extend for substantially the whole length of the anchor.

The anchor may be made of a bioabsorbable polymer, and preferably a bioabsorbable polymer and a bioactive filler. Alternatively the anchor may be manufactured from metal or a non bioabsorbable polymer such as PEEK.

The drive part of the driver may provide a sliding fit in the longitudinal opening in the anchor.

The drive part of the driver may extend substantially for the whole length of the longitudinal opening.

The engagement means may be located towards the distal end of the driver.

The engagement means may include a hole extending through the drive part. The engagement means may include a plurality of holes, and two holes may be provided, which holes may be longitudinally and/or circumferentially offset relative to each other.

The engagement means may include a slot, which slot may have a proximally inclined opening.

Alternatively the engagement means may be formed by crimping the distal end of the driver.

A distal exterior opening may be provided in the anchor, and the assembly may be arranged such that the ends of a loop of suture received in the engagement means extend out of said distal exterior opening.

In an alternative arrangement radial exterior openings are provided in the anchor extending radially outwardly from the longitudinal opening to the outside of the anchor, spaced from the distal end of the anchor. The driver may be arranged such that when the drive part is fully located in the longitudinal opening, the engagement means are aligned at least generally with the radial exterior openings. The distal end of the anchor may be substantially solid.

A further formation may extend for part or all of the length of the drive part to receive a suture therein to help prevent snagging of the suture during withdrawal of the drive part from the anchor.

The further formation may include a slot. The further formation may include an area of the drive part at the distal end thereof, of smaller cross section than the remainder of the drive part.

The driver may include an elongate part extending proximally from the drive part, and a recess formation may be provided extending longitudinally in the elongate part to receive sutures extending from the anchor. The formation may include a pair of diametrically opposite slots of a size to substantially fully receive a suture therein.

The invention also provides an anchor for a suture anchor assembly, the anchor being according to any of the preceding nineteen paragraphs.

The invention still further provides a driver for a suture anchor assembly, the driver being according to any of said preceding nineteen paragraphs.

The invention further provides a suture anchor assembly, the assembly including an anchor and a driver according to any of said preceding nineteen paragraphs and a suture extending through the drive part engagement means, and extending proximally from the exterior of the anchor.

The assembly may include two sutures each extending through the longitudinal opening in the body, and extending proximally from the exterior of the anchor.

The suture anchor assembly may be sterilised and provided in sterilised packaging.

The invention still further provides a method of attaching a suture to a bone, the method including forming a hole in the bone, locating a driver within an anchor, the driver and anchor being according to any of said preceding nineteen paragraphs, locating a suture extending through the longitudinal opening and out though the exterior opening of the anchor and extending longitudinally in a proximal direction, and locating the anchor in the bone hole by screwing the anchor into the hole using the driver.

The invention yet further provides a method of attaching a suture to a bone, the method including forming a hole in the bone, locating a driver within an anchor, the driver and anchor being according to any of said preceding nineteen paragraphs, locating a suture extending through the engagement means of the driver, with the ends of the suture passing out through the exterior opening of the anchor and extending longitudinally in a proximal direction, locating the anchor in the bone hole by screwing the anchor into the hole using the driver, withdrawing the driver together with the loop of suture formed by the suture extending through the engagement means from the anchor, and removing the suture from the driver engagement means.

The hole may be tapped prior to locating the anchor therein.

The suture may extend in the recess formation on the outside of the anchor and/or in the recess formation in the elongate part of the driver. The ends of the suture may be held on the elongate part of the driver during location of the anchor in the bone hole.

Needles may be attached to the ends of one or more of the sutures.

The ends of the sutures may be differently coloured to assist identification thereof.

Two sutures may be so located extending through the longitudinal opening, and each suture may be differently coloured or marked.

Embodiments of the present invention will now be described by way of example only and with reference to the accompanying drawings, in which:—

FIG. 6 is a diagrammatic side view of the end of the driver of the assembly of FIG. 1;

FIG. 7 is a similar view to FIG. 6 of a first alternative driver;

FIG. 8 is a similar view to FIG. 6 of a second alternative driver;

FIG. 9 is a cross sectional end view of the anchor of FIG. 1;

Figure 1:
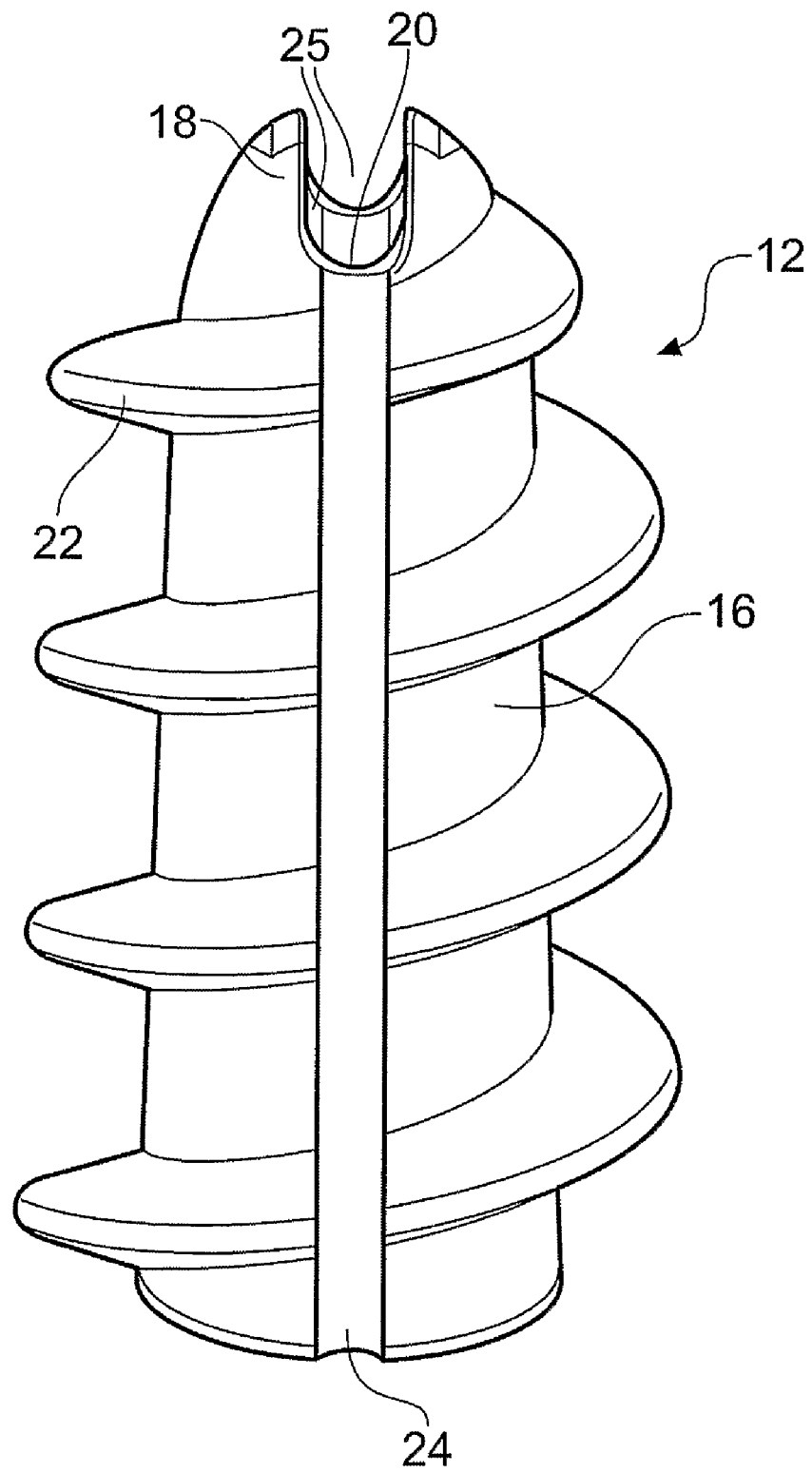
FIG. 1 is a diagrammatic side view of an anchor of a suture anchor assembly according to the invention.

FIGS. 1 to 6 and 9 show a suture anchor assembly 10 including an anchor 12 and a driver 14. The anchor 12 is made of a bioabsorbable polymer, and includes an essentially cylindrical body 16 which tapers gently to a rounded distal end 18. A longitudinal axial opening 20 of rectangular cross section is provided extending for the whole length of the anchor 12. Central recesses 19 are provided in each of the longer sides 21 of the rectangle of the opening 20.

A helical thread 22 is provided around the body 16 for the whole length thereof. A pair of diametrically opposite grooves 24 extend though the thread 22 and into the body 16 for the whole length thereof. The distal ends of the grooves 24 end in slots 25 in the distal end of the anchor 12. The grooves 24 are aligned with the longer sides of the rectangular cross section opening 20.

The driver 14 may typically be made of metal and includes a drive part 26 and a larger dimensioned handle part 28, only part of which is shown in the drawings. The drive part 26 is dimensioned such that when the anchor 12 is located on the driver 14, the proximal end of the anchor 12 substantially abuts against the distal end of the handle part 28.

Diametrically opposite longitudinal grooves 27 are provided in the handle part 28 extending from the drive part 26. The handle part 28 may take any suitable form to facilitate manipulation of the driver 14, and may include a contoured part to facilitate rotation thereof, or a formation to permit connection to a tool. The drive part 26 is of rectangular cross section so as to slidingly fit within the opening 20. An engagement means in the form of a through hole 30 is provided towards the distal end of the drive part 26. A thinner section part 32 extends distally from the hole 30.

Figure 2:
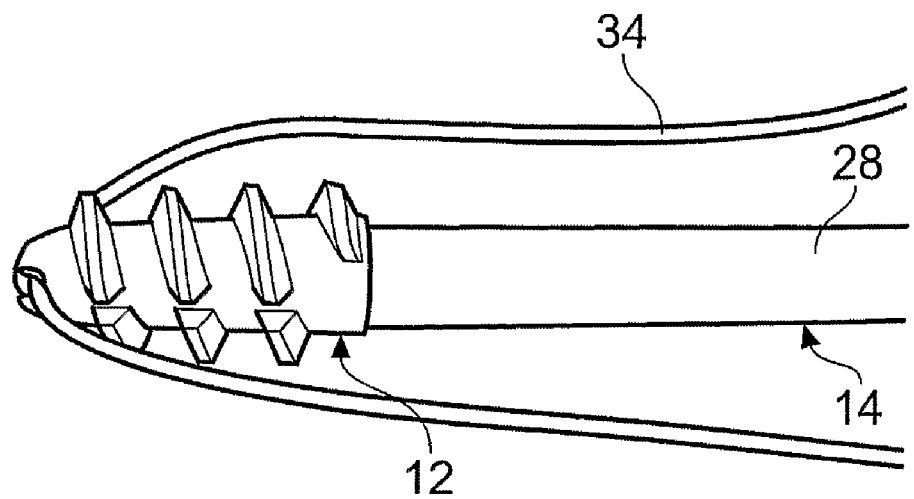
FIG. 2 is a diagrammatic side view of the assembly of FIG. 1 in a first condition.
Figure 3:
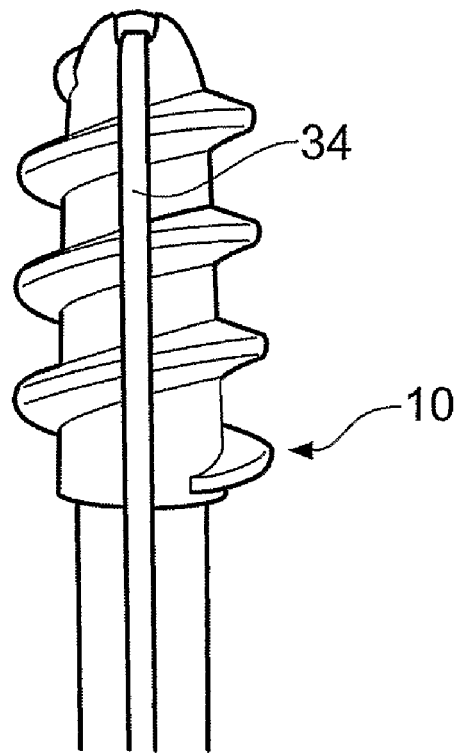
FIG. 3 is a diagrammatic side view of the assembly of FIG. 1 in a second condition.
Figure 4:
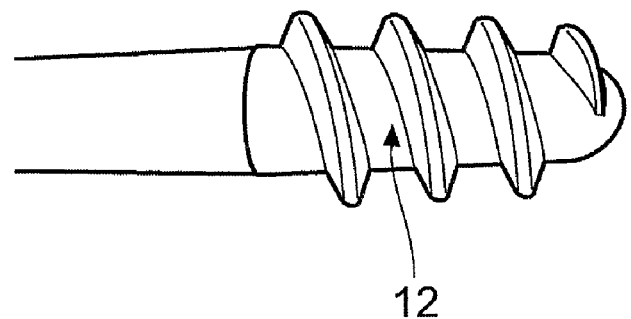
FIG. 4 is a similar view to FIG. 3 but with the assembly axially rotated through 90°.
Figure 5:
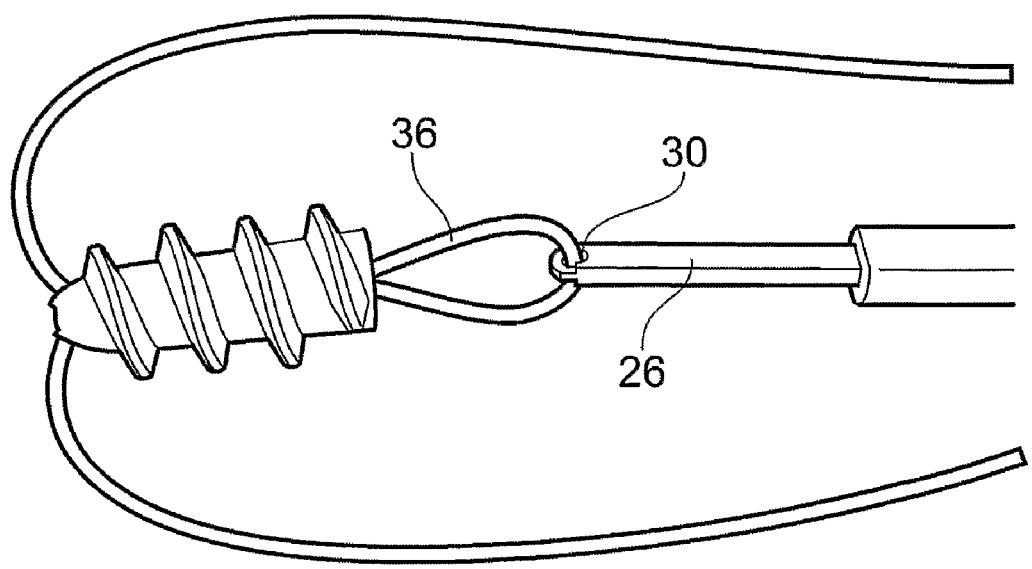
FIG. 5 is a diagrammatic view of the assembly of FIG. 1 in a third condition.

In use, the assembly 10 is assembled with a suture 34 as illustrated in FIGS. 2-5 of the drawings. The assembly 10 may be supplied pre loaded with the suture 34 in sterile packaging, or the suture could be arranged in the assembly 10 before use. The suture 34 extends in a loop 36, as shown in FIG. 5, through the opening 30, with the ends of the suture 34 extending from the loop 36 through the distal end 18 of the opening 20 as shown in FIG. 2.

In preparation for use, the suture 34 is located extending in the slots 24 and grooves 27, as shown in FIGS. 3 and 4. The suture 34 may be held in this position by bands, a sleeve, or similar extending around the handle part 28.

To use the assembly 10 to anchor the suture 34 to a bone, a hole is formed into the bone that is just longer than the anchor 12 and substantially as wide as the root diameter of the thread 22. The hole may be formed by drilling or punching. For polymeric screws such as the anchor 12, the hole may be tapped. The anchor 12 is then screwed into the hole using the driver 14 until the proximal end of the anchor 12 is substantially flush with the outer surface of the bone cortex.

The driver 14 and hence loop 36 can be withdrawn from the anchor 12, and when an adequate length of suture 34 has been pulled out, the loop 36 is cut to yield four free ends of suture 34 for use as required. This condition is illustrated in FIG. 5 prior to cutting.

There is thus described a suture anchor assembly and method of using same which provides for significant advantages. Provision of the thread 22 for the whole length of the anchor 12 maximises the contact area between the anchor 12 and bone thereby maximising the holding power of the anchor 12 in the bone. The absence of either a screw head or a suture eyelet on the proximal end of the anchor 12 enables the proximal end of the anchor 12 to be located flush with the outer surface of the cortical bone. As cortical bone is stronger than cancellous bone, this feature further enhances the fixation strength of the anchor in the bone and minimises the potential for anchor movement in the softer cancellous bone. The absence of a suture eyelet eliminates a major weak point particularly of prior polymeric anchors.

The longitudinal opening 20 extends for substantially the full length of the anchor 12, such that insertion torque from the driver 14 is applied to the anchor 12 substantially along the full length thereof. This is a particularly important feature for polymeric screws, where insertion torque applied for instance only at the proximal end, can result in either torsional failure of the screw or rotation of the driver in the drive recess as resistance to insertion is encountered. The grooves 24 mean that the presence of the suture 34 does not affect rotation of the anchor 12 in bone. The recesses 19 and thinner section part 32 accommodate the suture 34 to enable unobstructed withdrawal of the driver 14 from the anchor 12, following location of the anchor 12 in bone.

Various modifications may be made without departing from the scope of the invention. FIG. 7 shows an alternative arrangement for a driver 40 where instead of a through hole, a slot 42 is provided with a proximally inclined opening 44. Rather than a thinner section part a groove 46 extends distally from the closed end of the slot 42. This arrangement may ease threading of the suture on the assembly, and removes the need for cutting the suture loop to disengage the driver 14 following location of an anchor in bone.

FIG. 8 shows a further alternative driver 50 with a substantially square cross section drive part 52, two through holes 54, 56 are provided in the drive part 52, and the holes 54, 56 are offset longitudinally and also rotated by 90° relative to each other. This feature allows eight suture ends i.e. four sutures to be attached to each anchor. In this instance the distal end 58 of the drive part 52 is of reduced cross section to prevent snagging of the sutures between the driver 50 and an anchor. Obviously a corresponding anchor will be provided with a substantially square cross section longitudinal opening extending therethrough and two cross-slots or cross-holes to align with the corresponding holes in the driver.

Figure 10:
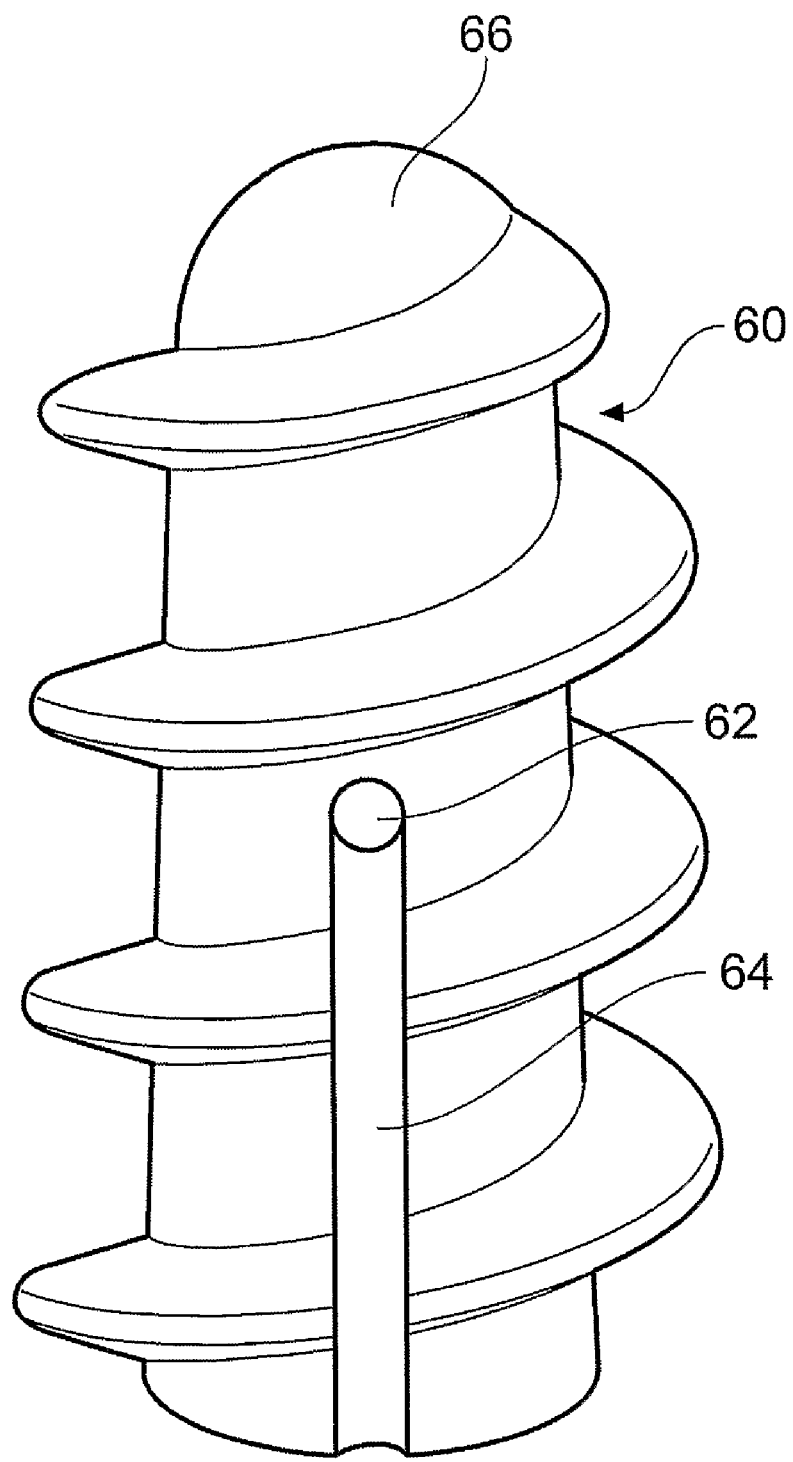
FIG. 10 is a similar view to FIG. 1 but of a first alternative anchor.

FIG. 10 shows a further anchor 60 which is similar to the anchor 12 except as follows. In this instance a pair of radial openings 62 are provided part way along the length of the anchor 60, and external respective grooves 64 extend proximally from the openings 62 to receive a suture therein. An appropriate driver (not shown) would be used with the anchor 60, which driver would have an opening to serve as a suture engagement means alignable with the opening 62 when the driver fully engages with the anchor 60. With such an arrangement the anchor 68 can have a closed distal end 66.

Figure 11:
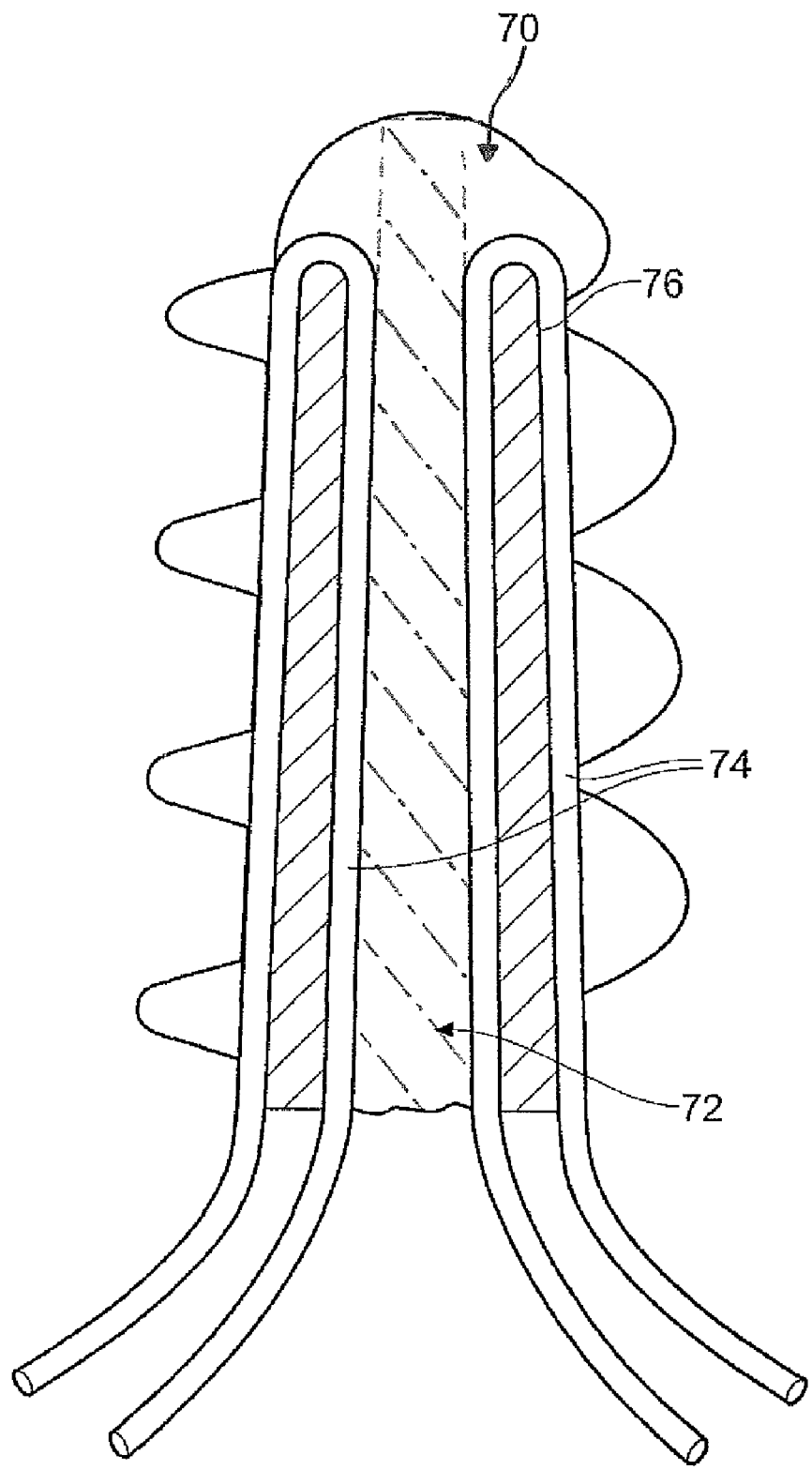
FIG. 11 is a cross-sectional view of a further alternative anchor and driver.
Figure 12:
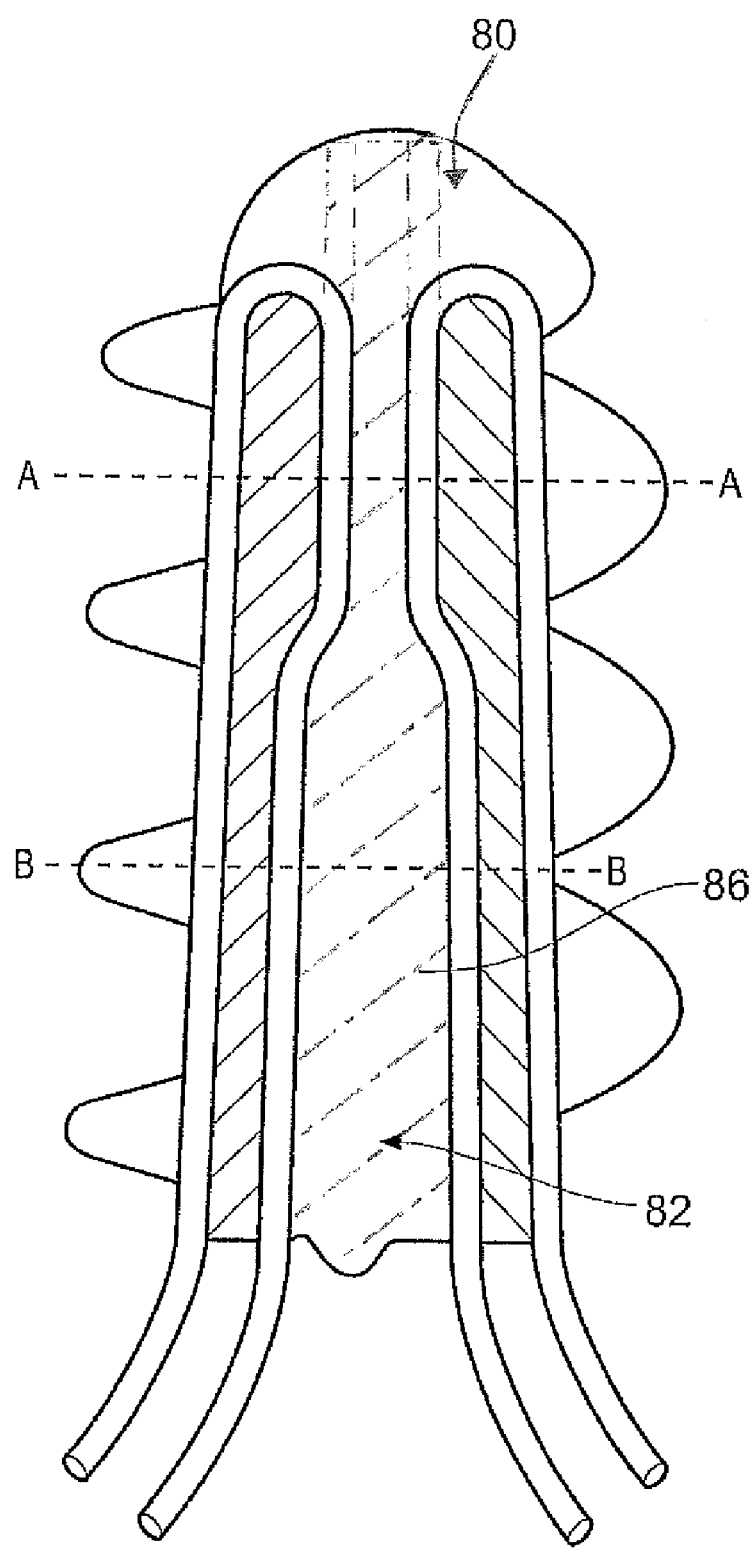
FIG. 12 is a similar view to FIG. 11 of a still further alternative anchor and driver.
Figure 13:
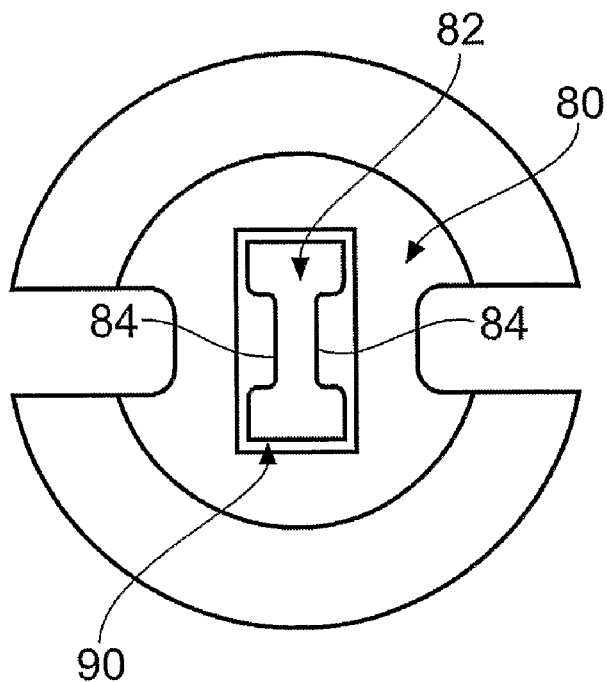
FIGS. 13 and 14 are respective end sectional views along the lines A-A and B-B of FIG. 12.
Figure 14:
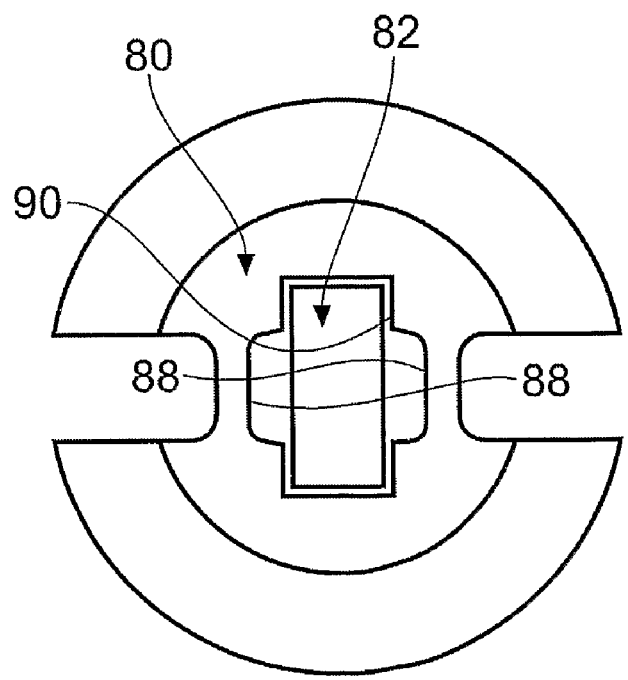

FIG. 11 shows a further anchor 70 with a driver 72. Only the drive part of the driver 72 has been shown. In this instance two sutures 74 are used, and each suture 74 may be differently coloured and/or braided/co-braided for identification. Each suture 74 extends up the inside of the anchor 70 through the longitudinal opening and out through an opening in the distal end thereof. The sutures 74 extend proximally from the distal end of the anchor 70 along longitudinal grooves 76 in the exterior of the anchor 70. The sutures 74 therefore provide four ends on which needles can be mounted if required.

Figure 15:
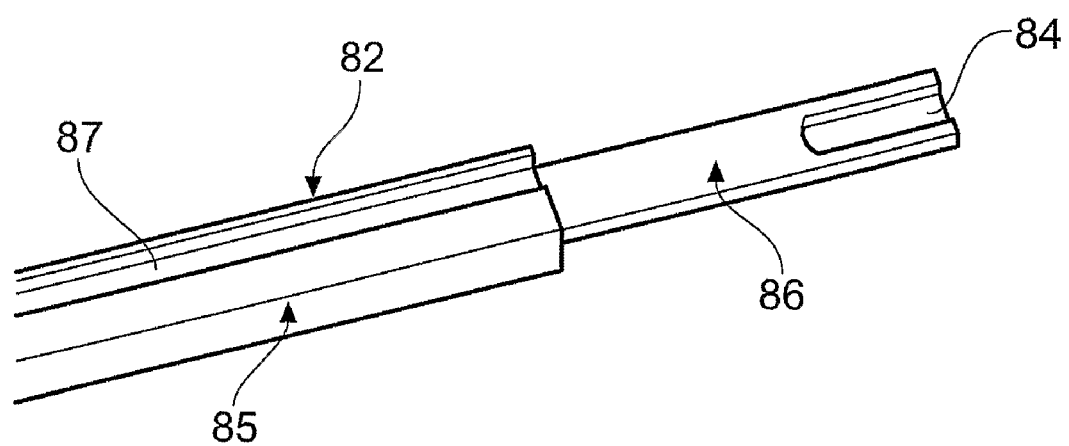
FIG. 15 is a diagrammatic perspective view of the end of the driver of FIG. 12.

FIGS. 12 to 15 show a still further anchor 80 with a driver 82. This arrangement is similar to the anchor 70 and driver 72 except as follows. As in FIG. 11, in FIG. 12 only the drive part 86 of the driver 82 is shown. FIG. 15 also shows the handle part 85 of the driver 82, which has grooves 87 similar to the grooves 27, for receiving respective sutures therein. When the anchor 80 is located on the driver 82, again the proximal end of the anchor 80 will substantially abut against the distal end of the handle part 85.

A groove 84 is provided on each side extending part way only along the drive part 86 from the distal end thereof. To coincide with the portion of the drive part 86 which does not have the groove 84, recesses 88 are provided in the side walls of the rectangular axial opening 90 through the anchor 80.

This arrangement permits a wider distal end of the anchor 80 where the suture engages and holds onto the anchor 80. At this point anchors can be prone to cutting by a suture in a "cheese wire" manner, and thus it is advantageous to have the extra width of material in the anchor 80 here. The proximal part of the drive part 86 is wider than the distal part, and this can help to prevent torsional failure of the drive part 86 as torque is supplied thereto during insertion of the anchor 80. Respective sutures can be received in the grooves 84 at the distal end of the driver 82, and in the recesses 88 at the proximal end of the anchor 80.

Figure 16:
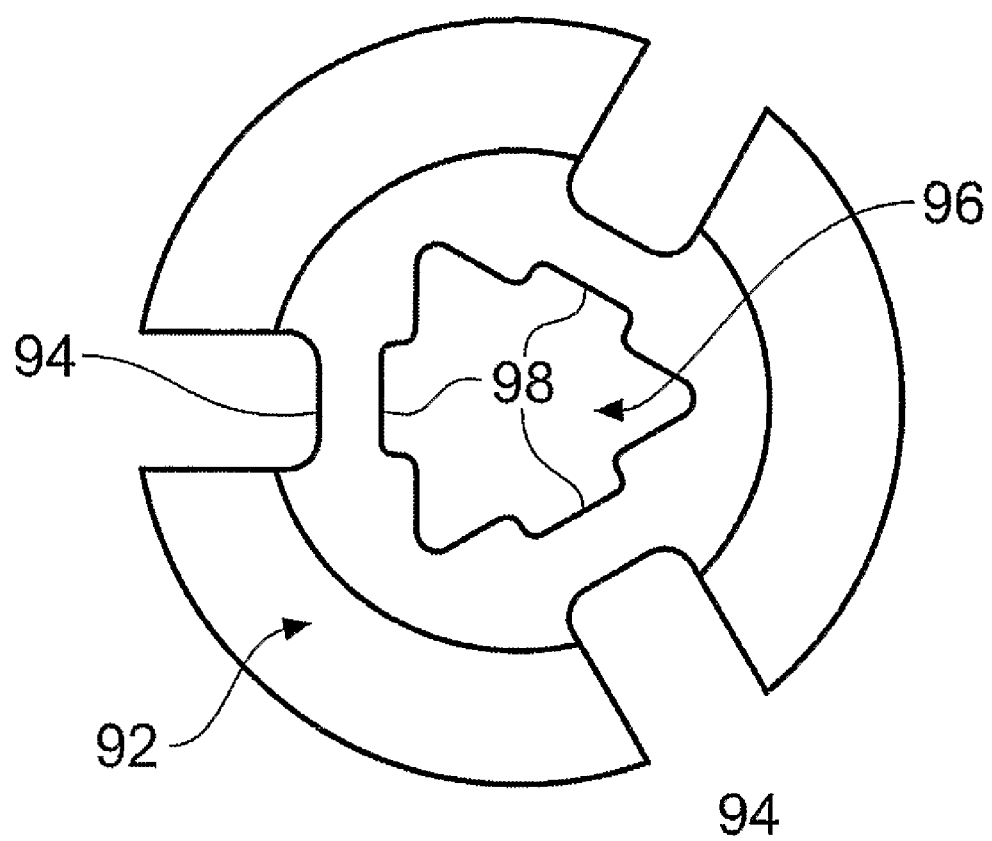
FIG. 16 is an end cross-sectional view of an alternative anchor.

FIG. 16 shows a further alternative anchor 92. The anchor 92 has three external grooves 94 to receive three sutures. This provides six suture ends giving a surgeon more placement options, thereby enabling a wider footprint of attachment of soft tissue to bone. The longitudinal axial opening 96 here has a generally triangular cross section, with recesses 98 provided in each side wall of the opening 96 to receive respective sutures. A corresponding driver (not shown) will be provided usable with the anchor 92. The driver will have a triangular cross section drive part, which may well include recesses therein to receive part of the sutures, with the remainder of the sutures being received in the recesses 98.

Various other modifications may be made without departing from the scope of the invention. For instance the material of the anchor may include a bioactive filler. Alternatively the anchor could be made of a non bioabsorbable polymer such as PEEK, or metal such as titanium alloy or stainless steel. The drive part and longitudinal openings could have further cross sectional shapes, and/or could taper inwardly towards the distal end. More than two holes or other formations could be provided in the driver to receive sutures.

The depth of the grooves below the root diameter in the anchors may be chosen to be less than the diameter of the sutures such that there is some protrusion of the sutures above the root diameter in order to provide frictional resistance to movement of the suture following deployment of the anchor, thus reducing the potential for fretting of the sutures. Where recesses are provided in the longitudinal opening extending through the anchors, such recesses may extend for the full length of the opening, or may only extend part way from the proximal end towards the distal end of the anchor.

The ends of the sutures may be coloured to assist identification thereof. Needles may be provided on the end of at least some of the sutures. Formations may be provided on the driver handle part to hold such needles prior to use.

It is to be realised that many of the above features could be combined as required. For instance the driver 50 may be suited for use with an anchor similar to the anchor 60, but obviously such an anchor would require four radial openings, and respective grooves.

Formations such as the recess in the sides of the longitudinal opening, or the grooves in the drive part, may extend for only part of the length of the respective component.

The engagement means at the distal end of the driver could be formed by crimping the distal end of the driver to hold the respective suture or sutures thereon, and the end of the driver could be bent over the suture or sutures. Arrangements with different numbers of sutures could be provided for instance a triangular configuration of grooves could be provided for use with three or perhaps six sutures.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. A suture anchor assembly, the assembly including an anchor locatable in a bone, a suture, and a driver selectively engageable with the anchor to enable rotation of the anchor, the anchor including a body with a helical screw thread on an exterior of the body, wherein the anchor is to be screwed into a pre-drilled hole in the bone, an opening extending longitudinally completely through the body and having a cross section of a non-circular, geometric shape, the driver including a drive part locatable within the opening of the anchor and profiled such that rotation of the driver causes rotation of the anchor, wherein the suture extends longitudinally completely through the opening of the anchor and a groove extends over only a distal part of a length of the drive part to receive the suture therein and at least one recess is provided in one or more side walls of the opening over only a proximal part of the length of the anchor body, to at least partially locate the suture in the at least one recess, wherein the recess substantially coincides with the portion of the drive part that does not have the groove.

2. An assembly according to claim 1, wherein a recess formation is provided on an outside of the anchor body which can receive two lengths of suture extending to a proximal end of the anchor.

3. An assembly according to claim 2, wherein the recess formation is dimensioned such that the suture does not extend substantially outwardly beyond a root of the thread when located in said formation.

4. An assembly according to claim 2, wherein the recess formation is dimensioned such that the suture does extend outwardly beyond a root of the thread when located in said formation to some extent.

5. An assembly according to claim 2, wherein the recess formation extends from a distal end of the opening of the anchor to the proximal end of the anchor.

6. An assembly according to claim 2, wherein the recess formation includes a longitudinal groove in the outside of the anchor body.

7. An assembly according to claim 2, wherein the recess formation includes a pair of longitudinal grooves, in the outside of the anchor body.

8. An assembly according to claim 7, wherein the longitudinal grooves are substantially diametrically opposite each other.

9. An assembly according to claim 1, wherein the opening in the anchor is generally rectangular in cross section.

10. An assembly according to claim 1, wherein the opening in the anchor is generally triangular in cross section.

11. An assembly according to claim 1, wherein the screw thread extends for substantially the whole length of the anchor.

12. An assembly according to claim 1, wherein the anchor is made of a bioabsorbable polymer.

13. An assembly according to claim 12, wherein the anchor is made of a bioabsorbable polymer and a bioactive filler.

14. An assembly according to claim 1, wherein the anchor is manufactured from metal or a non bioabsorbable polymer such as polyether ether ketone.

15. An assembly according to claim 1, wherein the drive part of the driver provides a sliding fit in the opening in the anchor.

16. An assembly according to claim 1, wherein the drive part of the driver extends substantially for the whole length of the opening in the anchor.

17. An assembly according to claim 1, wherein a distal exterior opening is provided in the anchor.

18. An assembly according to claim 1, wherein at least one exterior opening is provided extending through the anchor from the longitudinal opening to the exterior of the anchor, and the or each exterior opening is spaced from the distal end of the anchor and is radial of a longitudinal axis of the anchor.

19. An assembly according to claim 1, wherein the groove includes a slot.

20. An assembly according to claim 1, wherein the groove includes an area of the drive part at the distal end thereof, of smaller cross section than the remainder of the drive part.

21. An assembly according to claim 1, wherein the driver includes an elongate part extending proximally from the drive part.

22. An assembly according to claim 21, wherein the groove extends longitudinally in the elongate part of the driver to receive the suture extending from the anchor.

23. An assembly according to claim 22, wherein a pair of diametrically opposite grooves each of a size to substantially fully receive the suture therein extend longitudinally in the elongate part of the driver.

24. An assembly according to claim 1, wherein the groove extends over only a distal part of the length of the drive part of the driver and the recess is provided over only a proximal part of the length of the opening.

* * * * *